(12) United States Patent
Meidler et al.

(10) Patent No.: US 9,896,716 B2
(45) Date of Patent: Feb. 20, 2018

(54) PROTEIN ASSAY

(71) Applicants: Omrix Biopharmaceuticals Ltd., Rehovot (IL); Ethicon, Inc., Somerville, NJ (US)

(72) Inventors: Roberto Meidler, Rehovot (IL); Anne J. Gorman, Hightstown, NJ (US); Israel Nur, Moshav Timmorim (IL); Liliana Bar, Rehovot (IL); Ashley DeAnglis, Skillman, NJ (US)

(73) Assignees: Ethicon, Inc., Somerville, NJ (US); Omrix Biopharmaceuticals Ltd., Rehovot (IL)

( * ) Notice: Subject to any disclaimer, the term of this patent is extended or adjusted under 35 U.S.C. 154(b) by 0 days.

(21) Appl. No.: 14/930,799

(22) Filed: Nov. 3, 2015

(65) Prior Publication Data

US 2016/0053299 A1 Feb. 25, 2016

Related U.S. Application Data

(62) Division of application No. 12/298,814, filed on Oct. 28, 2008, now Pat. No. 9,213,035.

(30) Foreign Application Priority Data

May 22, 2008 (WO) .................. PCT/US2008/06451

(51) Int. Cl.
*G01N 33/86* (2006.01)
*C12Q 1/56* (2006.01)
*G01N 33/68* (2006.01)

(52) U.S. Cl.
CPC .............. *C12Q 1/56* (2013.01); *G01N 33/68* (2013.01); *G01N 33/86* (2013.01)

(58) Field of Classification Search
None
See application file for complete search history.

(56) References Cited

U.S. PATENT DOCUMENTS

| | | | |
|---|---|---|---|
| 4,692,406 A | 9/1987 | Becker et al. | |
| 5,110,727 A | 5/1992 | Oberhardt | |
| 5,292,664 A | 3/1994 | Fickenscher | |
| 5,589,571 A | 12/1996 | King | |
| 5,851,836 A | 12/1998 | Enomoto | |
| 6,448,024 B1 | 9/2002 | Bruegger | |
| 8,133,696 B2 | 3/2012 | Giesen et al. | |
| 9,213,035 B2 * | 12/2015 | De Anglis | C12Q 1/56 |

FOREIGN PATENT DOCUMENTS

| | | |
|---|---|---|
| CA | 2096215 | 11/1993 |
| CN | 1763219 | 4/2006 |
| CN | 101059521 | 10/2007 |
| DE | 3330699 | 8/1983 |
| EP | 0587398 | 1/1998 |
| EP | 0570354 | 9/1998 |
| EP | 0815139 | 11/2001 |
| EP | 1559438 | 11/2010 |
| JP | 03-98598 | 4/1991 |
| JP | 06-046898 | 6/1994 |
| JP | 06-209794 | 8/1994 |
| JP | 09-266798 | 10/1997 |
| JP | 11-160321 | 6/1999 |
| NO | 309902 | 4/2001 |
| SU | 1161878 | 6/1985 |
| SU | 1767425 | 10/1992 |
| WO | WO 2006/089697 | 8/2006 |
| WO | WO 2007/127834 | 11/2007 |
| WO | WO 2009/142638 | 11/2009 |

OTHER PUBLICATIONS

Barrow, Rachel T. 'Inhibition by Heparin of Thrombin-catalyzed Activation of the Factor VIII—von Willebrand Factor Complex' The Jouurnal of Biological Chemistry (1994) vol. 269, No. 1 pp. 593-598.
Gaffney, P.J. et al 'Problems in the Assay of Thrombin Using Synthetic Peptides as Substrates' Thrombosis Research (1977) vol. 10 pp. 549-556.
Hatton, M.W.C. 'Deendothelialization In Vivo Initiates a Thrombogenic Reaction at the Rabbit Aorta Surface' American Journal of Pathology (1989) vol. 135, No. 3 pp. 499-508.
Martin, B.M. et al 'Equilibrium Binding of Thrombin to Platelets' Biochemistry (1976) vol. 15, No. 22 pp. 4886-4893.
Scheraga, H.A. 'The Thrombin-Fibrinogen Interaction' Biophysical Chemistry, vol. 112, No. 2-3, Dec. 20, 2004, pp. 117-130.
Stone, S.R. et al Mechanistic Studies on Thrombin Catalysis Biochemistry (1991) vol. 30, pp. 9841-9848.
Vermylen, C., et al 'A Rapid Enzymatic Method for Assay of Fibrinogen Fibrin Polymerization Time (FPT Test)' Clinica Chimica Acta, vol. 8, No. 3 May 1, 1963 pp. 418-424.
Zhang, Ying 'Detection of Thrombin Activity and the Clinical Significance thereof' Microcirculation vol. 15, No. 2 pp. 70-72.
International Search Report re: PCT/US2008/064514 dated Feb. 17, 2009.
Partial European Search Report re: EP09251374 dated Sep. 16, 2009.
Katzel, R. et al., 'Kinetic determination of fibrinogen with batroxobin (reptilase)' Journal of Comprehensive Internal Medicine (1991) vol. 46, pp. 349-424.
Sturzebecher, J. et al., 'Inhibition of Batroxobin, A Serine Proteinase from Bothrops Snake Venom, by Derivatives of Benzamidine' Toxicon (1986) vol. 24, No. 6 pp. 585-595.

* cited by examiner

*Primary Examiner* — Hope Robinson
(74) *Attorney, Agent, or Firm* — David R. Crichton

(57) ABSTRACT

A method is described for the measurement of thrombin activity in the presence of fibrinogen, or for the measurement of the functionality of fibrinogen in the presence of thrombin.

3 Claims, 1 Drawing Sheet

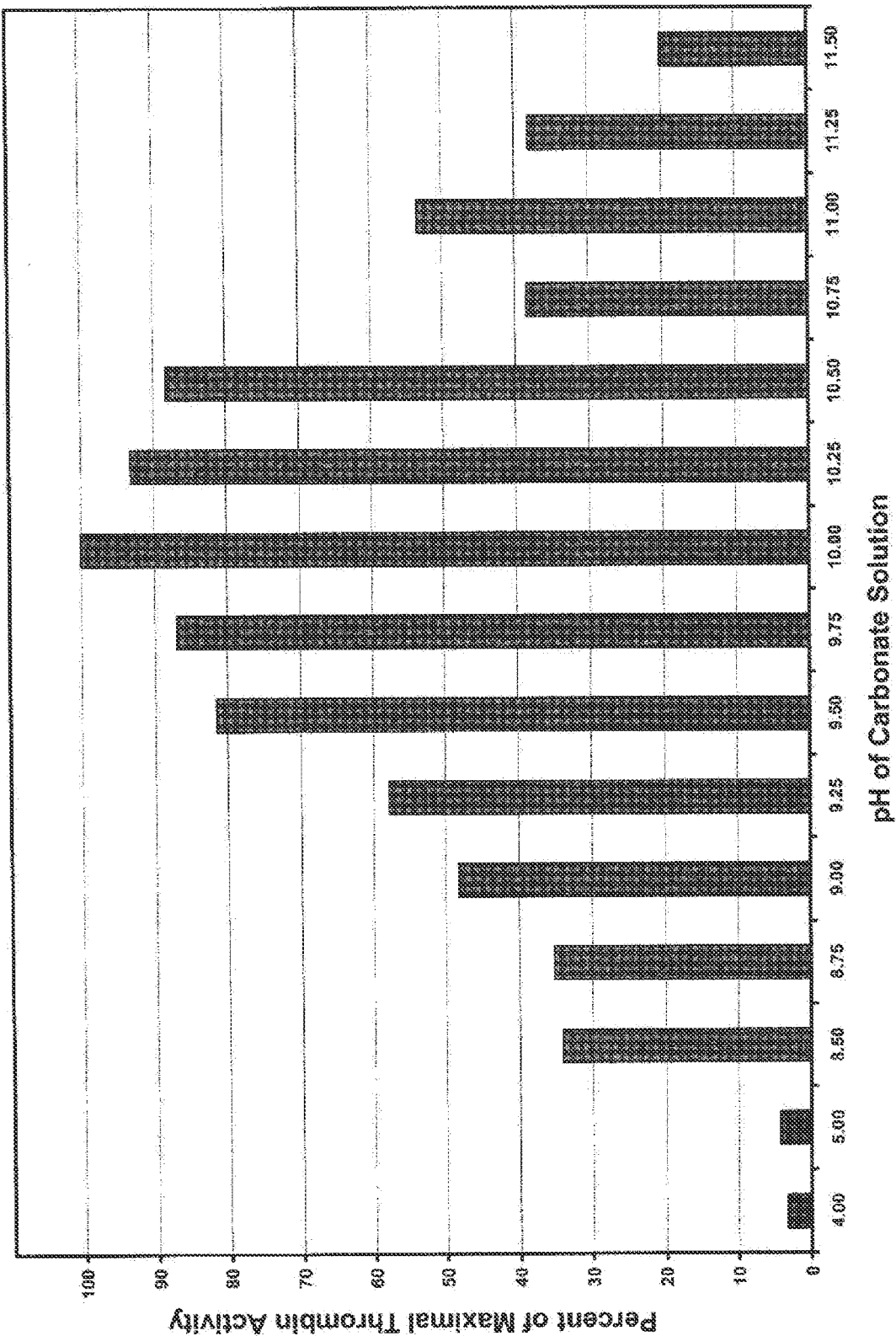

PROTEIN ASSAY

FIELD OF THE INVENTION

A method is described for the measurement of thrombin activity in the presence of fibrinogen, or for the measurement of the functionality of fibrinogen in the presence of thrombin.

BACKGROUND OF THE INVENTION

Fibrinogen and thrombin are critical proteins involved in achieving hemostasis after vascular injury and essential to blood clot formation. Fibrinogen and thrombin can be combined in powder form or in a non-aqueous suspension, without initiating a typical clotting reaction, thus preventing the formation of a fibrin clot until the proteins are hydrated in an aqueous medium or other liquid environment in which the proteins are soluble. An admixture of these proteins in powder form have a variety of potential biomedical applications including topical hemostasis, tissue repair, drug delivery, etc. In addition, an admixture of these proteins may be loaded onto a carrier or substrate, or other medical device, in powder form to form a product that may be used for example as a hemostatic device.

The clotting activity of thrombin is usually measured by combining thrombin in solution with a known amount of fibrinogen in solution. With appropriate conditions, the rate of clot formation after combining the two proteins is dependent on the activity of the thrombin. The rate of clot formation of a sample with an unknown amount of thrombin is compared with the rate of clot formation of a thrombin reference or thrombin standard to determine the activity of the sample.

Thrombin activity is a critical attribute of any thrombin/fibrinogen product and will dictate its functionality. Although the measurement of free thrombin is straightforward, measurement of thrombin activity when thrombin and fibrinogen are in an unreacted admixture has been a challenge since measurement thereof typically requires that the admixture of proteins be hydrated and solubilized, and fibrin clot formation between solubilized thrombin and fibrinogen immediately initiates upon hydration. Furthermore, since thrombin is known to bind and interact specifically with the immediately formed fibrin clot, the thrombin becomes bound in the fibrin clot and is no longer freely soluble in the hydrating solution and becomes unavailable for subsequent measurement of thrombin activity. Hence, any resultant measurement of the thrombin activity of any thrombin/fibrinogen product via hydration and clot formation is only partial and hence inaccurate.

Moreover, when the proteins are in an unreacted admixture and loaded onto a carrier, substrate or medical device, it may be necessary to remove the proteins from the substrate to accurately measure the thrombin activity, for example, if the carrier, substrate or medical device adversely affects the measurement of the activity or functionality of the proteins due to physical, chemical or optical interference with the measurement detection system. To overcome interference from the carrier, substrate or medical device, removal or extraction of the proteins must be performed without exposing the admixture to aqueous conditions, which would result in clot formation preventing subsequent measurement.

Fibrinogen is most frequently measured by a method originally described by Clauss, which measures fibrinogen functionality based on the rate of clot formation. In a typical Clauss assay, a sample with an unknown amount of soluble fibrinogen is combined with an excess of thrombin. The proportions of fibrinogen and thrombin are such that fibrinogen is the rate limiting reactant and the rate of clot formation is a function of the fibrinogen concentration. A fast clotting time would be indicative of a high fibrinogen concentration. Conversely, a longer dotting time would indicate a low concentration of functional fibrinogen. The amount of functional fibrinogen can be quantified by comparing the clotting time of the sample with those of a series for standards to establish a standard curve. The concentration of fibrinogen in the sample can be determined mathematically based on the equation derived from the clotting times of the standards.

While measurement of free fibrinogen in solution, e.g., human plasma, can be performed by established methods, assessment of fibrinogen functionality when fibrinogen is in the presence of thrombin has been a challenge. Hydration of the admixture will result in thrombin-mediated conversion of fibrinogen into an insoluble fibrin clot. Once fibrin is generated, any subsequent measurement of fibrinogen is no longer possible since the release of the fibrinopeptides from fibrinogen resulting in fibrin formation is essentially irreversible.

Hence there remains a need to accurately measure the activity of thrombin in the presence of fibrinogen, and to measure the functionality of fibrinogen in the presence of thrombin.

DETAILED DESCRIPTION OF THE DRAWINGS

FIG. 1 shows the influence of pH of the inactivation solution on recovered thrombin activity.

SUMMARY OF THE INVENTION

Described herein is a method for determining the activity or functionality of either a first reactive component or a second reactive component in an admixture of the first reactive component and the second reactive component, comprising the steps of (a) reversibly inhibiting the first reactive component to yield a mixture having an inactivated first reactive component and the second reactive component; (b) adding to the mixture an excess of the second reactive component when evaluating the activity of the first reactive component, or an excess of the first reactive component when evaluating the activity of the second reactive component; (c) reversibly activating the first reactive component; (d) allowing the first reactive component to react with the second reactive component in the mixture and the excess of the second reactive component, or allowing the first reactive component to react with the second reactive component in the mixture and the excess of the first reactive component; and (e) determining the activity or functionality of first or second reactive component originally present in the dry mixture.

DETAILED DESCRIPTION OF THE INVENTION

As discussed above, in order to determine the thrombin activity of an unreacted admixture of thrombin and fibrinogen, for example in powder form or a non-aqueous suspension such as an ethanol suspension, it is necessary to rehydrate the proteins and for the thrombin and fibrinogen to be solubilized in the hydrating medium, to obtain an accurate measurement of the thrombin activity. However, once the admixture is contacted with the hydrating medium, any solubilized thrombin and fibrinogen will react to form an immediate clot, and any available thrombin will bind to the clot and will not be freely available for the measurement thereof.

In one embodiment, the thrombin activity of the unreacted admixture is temporarily inhibited or reversibly inhibited, thereby preventing the formation of a fibrin clot until the thrombin and fibrinogen are completely solubilized. By inhibiting thrombin activity, immediate clot formation is avoided and the thrombin is able to freely dissolve in an aqueous hydrating medium and remains available for measurement.

The temporary or reversible inhibition of thrombin activity can be achieved, for example, by adjusting the alkaline environment of the thrombin. For example, this may be accomplished by reconstituting or hydrating an unreacted admixture of thrombin and fibrinogen in an inhibitory or inactivation solution, i.e., an alkaline solution having a pH ranging from about 8.5 to 11.5, preferably from about 9.5 to 10.5, and more preferably about 10, to form a first solution. Table 1 shows the effect of pH on the recovered activity of thrombin. Maximal recovered thrombin activity was observed when the alkalinity of the inactivation solution was at pH 10. Within a pH range of 9.5-10.5, at least 80% of the maximal recovered thrombin activity was achieved. At pH levels less than 9.5 and greater than 10.5, the maximal recovered thrombin activity decreased as the pH level deviated further from 10. At pH levels of 9.25 and lower, evidence of clot formation was observed during hydration and may explain the reduced maximal recovered thrombin activity that is observed at lower pH values approaching neutral conditions. In acidic conditions, for example of pH 4 and 5, maximal recovered thrombin activity was significantly less than that observed with alkaline conditions, which may be an indication of the irreversible inactivation of the thrombin.

The inhibitory or inactivation solution may be an alkaline solution or a buffered alkaline solution, including but not limited to a solution of carbonate, TRIS base, borate, glycine, phosphate, methylamine, 2-(Cyclohexylamino)ethanesulfonic acid (CHES), 3-(Cyclohexylamino)-1-propanesulfonic acid (CAPS) or 3-(Cyclohexylamino)-2-hydroxy-1-propanesulfonic acid (CAPSO).

Once the thrombin and fibrinogen are completely solubilized in the inhibitory or inactivation solution, the first solution or a portion thereof may be combined with a known amount of fibrinogen in a second solution, preferably having an excess amount of fibrinogen to form a third solution, while maintaining the pH at about 8.5 to 11.5, preferably from about 9.5 to 10.5, and more preferably about 10. An excess of fibrinogen is utilized so that the amount of thrombin in the admixture is the rate limiting reactant in the formation of the fibrin clot, to ensure that the activity of thrombin correlates strongly with the rate of clot formation. If fibrinogen is not in excess, the rate of clotting would be dependent upon both thrombin and fibrinogen.

Thereafter, the thrombin activity may be reversed, for example, by adjusting the pH of the third solution to a range where the thrombin activity is no longer inhibited, i.e., from about 6.0 to less than 8.5, preferably from about 7.0 to less than 8.5, and more preferably about 7.5. Alternatively, the inactivation solution having the solubilized proteins or a portion thereof, i.e., the first solution, may be combined with an known amount of fibrinogen in a second solution, preferably an excess amount of fibrinogen, to form a third solution whereby the inhibition of the thrombin activity is simultaneously reversed. Examples of the second solution include but are not limited to buffer solutions for TRIS-HCl, imidazole, 4-(2-Hydroxyethyl)piperazine-1-ethanesulfonic acid (HEPES), phosphate, barbital, 4-Morpholinepropanesulfonic acid (MOPS), 3-Morpholino-2-hydroxypropanesulfonic acid (MOPSO), 1,4-Piperazinediethanesulfonic acid (PIPES), N,N-Bis(2-hydroxyethyl)-2-aminoethanesulfonic acid (BES), citrate or carbonate.

The volume and buffering capacity of the second solution should be sufficient to result in a third solution having a pH from about 6.0 to less than 8.5, preferably from about 7.0 to less than 8.5, and more preferably about 7.5, when added to the first solution. For example, the ratio of the volumes of the first and second solutions typically ranges from about 1:1 to 1:20, and preferably is about 1:4 to 1:10, for example, when the molarity of the second solution is about 25 mM to 500 mM TRIS-HCl buffer, and preferably about 100 mM to 150 mM TRIS-HCl buffer.

The thrombin activity may be determined using a coagulation analyzer with a mechanical endpoint detection system to detect clot formation, such as the Diagnostica Stago ST4 Coagulation Analyzer, or a device that measures changes in turbidity due to fibrin clot formation. The solubilized proteins in the inactivation solution may be combined with the second solution in one of these devices, and the time to coagulation may be measured, which can then be correlated to the clotting times for known thrombin activities.

Another method by which thrombin activity can be measured is using a chromogenic or fluorogenic peptide substrate for thrombin. In this method, solubilized thrombin is combined with an excess of chromogenic or fluorogenic substrate. Thrombin will cleave the substrate releasing a chromophore or fluorophore which can be monitored in a spectrophotometer or fluorimeter. Examples of chromogenic or fluorogenic substrates include, β-Ala-Gly-Arg-p-nitroanilide diacetate and Z-Gly-Pro-Arg-AMC [Z=Benzyloxycarbonyl; AMC=7-amino-4-methylcoumarin], respectively. The rate of released chromophore or fluorophore can be correlated to the activity of thrombin.

In another embodiment, the functionality of the fibrinogen in an unreacted admixture with thrombin may be measured by inhibiting the thrombin activity by adjusting the alkaline environment of the thrombin. For example, this may be accomplished by reconstituting or hydrating an admixture of thrombin and fibrinogen in an inhibitory or inactivation solution, i.e., an alkaline solution having a pH ranging from about 8.5 to 11.5, preferably from about 9.5 to 10.5, and more preferably about 10, to form a first solution. The inhibitory or inactivation solution may be an alkaline solution or a buffered alkaline solution, including but not limited to a solution of carbonate, TRIS(Tris(hydroxymethyl)aminomethane) base, borate, glycine, phosphate, methylamine, 2-(Cyclohexylamino)ethanesulfonic acid (CHES), 3-(Cyclohexylamino)-1-propanesufonic acid (CAPS) or 3-(Cyclohexylamino)-2-hydroxy-1-propanesulfonic acid (CAPSO). Additionally and optionally, a thrombin inhibitor such as Bivalirudin (Angiomax) may be added to the inhibitory or inactivation solution or the first solution to achieve maximum inhibition of thrombin activity thus allowing most of the fibrinogen to be solubilized for subsequent testing. Other examples of thrombin inhibitors include antithrombin, heparin, low molecular weight heparin, low molecular weight heparin analogs, argatroban, melagatran, efegatran, inogatran, dabigatran, hirudan and derivatives of hirudan such as Lepirudin, and Desirudin.

Once the thrombin activity has been inhibited, the functionality of fibrinogen can be determined by combining the first solution or a portion thereof with a known amount of thrombin in a second solution, preferably having an excess amount of thrombin to form a third solution, while maintaining the pH at about 8.5 to 11.5, preferably from about 9.5 to 10.5, and more preferably about 10. An excess of thrombin is utilized so that the amount of fibrinogen in the admixture is the rate limiting reactant in the formation of the fibrin dot, to ensure that the concentration of fibrinogen correlates strongly with the rate of clot formation. If thrombin is not in excess, the rate of clotting would be dependent upon both thrombin and fibrinogen.

Thereafter, the thrombin activity may be reversed, for example, by adjusting the pH of the third solution to a range where the thrombin activity is no longer inhibited, i.e., from about 6.0 to less than 8.5, preferably from about 7.0 to less than 8.5, and more preferably about 7.5. Alternatively, the inactivation solution having the solubilized proteins or a portion thereof, i.e., the first solution, may be combined with an known amount of thrombin in a second solution, preferably an excess amount of thrombin, to form a third solution whereby the inhibition of the thrombin activity is simultaneously reversed. Examples of the 10 second solution include but are not limited to buffer solutions for TRIS-HCl, imidazole, 4-(2-Hydroxyethyl)piperazine-1-ethanesulfonic acid (HEPES), phosphate, barbital, 4-Morpholinepropanesufonic acid (MOPS), 3-Morpholino-2-hydroxypropanesulfonic acid (MOPSO), 1,4-Piperazinediethanesulfonic acid (PIPES), N,N-Bis(2-hydroxyethyl)-2-aminoethanesulfonic acid (BES), citrate or carbonate at pH of about 7.5.

The functionality of the fibrinogen may be determined using a coagulation analyzer with a mechanical endpoint detection system to detect clot formation, such as the Diagnostica Stago ST4 Coagulation Analyzer, or a device that measures changes in turbidity due to fibrin clot formation. The solubilized proteins in the inactivation solution may be combined with the second solution in one of these devices, and the time to coagulation may be measured, which can then be correlated to the clotting times for known fibrinogen functionalities.

Alternatively, the fibrinogen functionality may be determined by inhibiting the thrombin activity using a thrombin inhibitor such as Bivalirudin (Angiomax). Optionally, the alkaline environment of the thrombin may be adjusted in combination with the use of the thrombin inhibitor. Other examples of thrombin inhibitors include antithrombin, heparin, low molecular weight heparin, low molecular weight heparin analogs, argatroban, melagatran, efegatran, inogatran, dabigatran, hirudan and derivatives of hirudan such as Lepirudin, and Desirudin. Once the thrombin activity is inhibited, the fibrinogen functionality may be determined by using a thrombin-like enzyme that is capable of acting on fibrinogen to form a clot, but is unaffected by the thrombin inhibitor. Examples of thrombin-like enzymes include but are not limited to Batroxobin (derived from the venom of the South American pit viper Bothrops atrox) and Ancrod (derived from the venom of Calloselasma rhodostoma).

In the event the proteins are in an unreacted admixture and loaded onto a carrier, substrate or medical device, for example, the admixture may be in powder form where the proteins are dry or dried, removal of the proteins prior to rehydration and solubilization may be performed by extracting the proteins using a non-aqueous liquid, including but not limited to perfluorinated hydrocarbons such as HFE-7000, HFE7001, HFE7003, HFE-7300 and PF-5060 (commercially available from 3M of Minnesota) and any other carrier fluid in which the proteins do not dissolve may be used, such as alcohols, ethers or other organic fluids. Once the proteins have been extracted using the non-aqueous solvent, the thrombin activity or fibrinogen functionality may be measured as described above.

Alternatively, where the proteins are loaded onto a carrier, substrate or medical device, the thrombin activity or fibrinogen functionality may be determined as described above without removal of the proteins. For example, the proteins may be hydrated by placing the carrier, substrate or medical device having the proteins thereon directly in the inhibitory or inactivation solution which can be sampled for testing for thrombin activity or fibrinogen functionality as described above.

We claim:

1. A method for determining the functionality of fibrinogen in a mixture of unreacted thrombin and unreacted fibrinogen in powder form or a non-aqueous suspension, comprising the steps of:
    (a) inhibiting the thrombin to yield a mixture having fibrinogen and inactivated thrombin by adding an inhibitory solution having a pH ranging from 8.5 to 11.5;
    (b) adding to the mixture in step (a) an activating solution comprising an additional amount of thrombin and having a pH ranging from about 6.0 to less than 8.5;
    (c) allowing the thrombin to react with the fibrinogen; and
    (d) determining the functionality of fibrinogen.

2. The method of claim 1, wherein step (a) comprise adding a thrombin inhibitor.

3. The method of claim 2, wherein the thrombin inhibitor is selected from the group consisting of antithrombin, heparin, low molecular weight heparin fondaparinux, argatroban, melagatran, efegatran, inogatran, dabigatran, bivalirudin, Lepirudin, and Desirudin.

* * * * *